(12) United States Patent
Mueller et al.

(10) Patent No.: US 8,287,536 B2
(45) Date of Patent: Oct. 16, 2012

(54) CUTTING ASSEMBLY FOR SURGICAL INSTRUMENTS

(75) Inventors: Peter M. Mueller, Frederick, CO (US); Sara E. Anderson, Erie, CO (US)

(73) Assignee: TYCO Healthcare Group LP, Mansfield, MA (US)

(*) Notice: Subject to any disclaimer, the term of this patent is extended or adjusted under 35 U.S.C. 154(b) by 526 days.

(21) Appl. No.: 12/548,031

(22) Filed: Aug. 26, 2009

(65) Prior Publication Data

US 2011/0054467 A1 Mar. 3, 2011

(51) Int. Cl.
*A61B 18/12* (2006.01)

(52) U.S. Cl. .............................. 606/51; 606/46

(58) Field of Classification Search .................. 606/41, 606/45–52
See application file for complete search history.

(56) References Cited

U.S. PATENT DOCUMENTS

| | | | |
|---|---|---|---|
| 2,031,682 A * | 2/1936 | Wappler et al. ............. | 606/46 |
| 4,129,277 A | 12/1978 | Tenniswood | |
| 5,201,741 A | 4/1993 | Dulebohn | |
| 5,711,144 A | 1/1998 | Pea | |
| 5,971,983 A * | 10/1999 | Lesh ............................ | 606/41 |
| 6,050,995 A * | 4/2000 | Durgin ........................ | 606/47 |
| 6,273,887 B1 | 8/2001 | Yamauchi et al. | |
| 6,616,654 B2 * | 9/2003 | Mollenauer ................. | 606/28 |
| 6,786,905 B2 | 9/2004 | Swanson et al. | |
| 6,953,461 B2 | 10/2005 | McClurken et al. | |
| 7,234,292 B1 | 6/2007 | O'Rourke et al. | |
| 8,016,827 B2 | 9/2011 | Chojin | |
| 8,114,122 B2 | 2/2012 | Nau, Jr. et al. | |
| 8,142,473 B2 | 3/2012 | Cunningham et al. | |
| 8,162,973 B2 | 4/2012 | Cunningham et al. | |
| 2002/0165534 A1 | 11/2002 | Hayzelden et al. | |
| 2003/0171747 A1 | 9/2003 | Kanehira et al. | |
| 2007/0078459 A1* | 4/2007 | Johnson et al. ............. | 606/51 |
| 2008/0195093 A1 | 8/2008 | Couture et al. | |
| 2009/0198233 A1 | 8/2009 | Chojin et al. | |
| 2009/0209957 A1 | 8/2009 | Schmaltz et al. | |

(Continued)

FOREIGN PATENT DOCUMENTS

CA 2104423 2/1994

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley (57) ABSTRACT

The present disclosure relates to an end effector assembly for use with a forceps. The end effector assembly includes a pair of jaw members and a cutting element. The pair of jaw members having at least one jaw member that is moveable relative to the other from a first, open position to a second, closed position for grasping tissue. Each of the jaw members includes a cutting channel that is defined therein and extends therealong. The cutting element includes a fixed end and a movable end. The fixed end is disposed within the cutting channel of one of the jaw members and the moveable end is disposed within the cutting channel of the other of the jaw member. The cutting element defines a movable cutting loop disposed between the cutting channels and between the fixed end and the movable end. The cutting loop has an arcuate portion that is reciprocatable to cut tissue.

2 Claims, 5 Drawing Sheets

U.S. PATENT DOCUMENTS

| | | | |
|---|---|---|---|
| 2009/0209960 A1 | 8/2009 | Chojin et al. |
| 2009/0234354 A1 | 9/2009 | Johnson et al. |
| 2009/0248021 A1 | 10/2009 | McKenna et al. |
| 2010/0016857 A1 | 1/2010 | McKenna et al. |
| 2010/0036375 A1 | 2/2010 | Regadas et al. |
| 2010/0042140 A1 | 2/2010 | Cunningham et al. |
| 2010/0042143 A1 | 2/2010 | Cunningham et al. |
| 2010/0049187 A1 | 2/2010 | Carlton et al. |
| 2010/0057081 A1 | 3/2010 | Hanna et al. |
| 2010/0057082 A1 | 3/2010 | Hanna et al. |
| 2010/0057083 A1 | 3/2010 | Hanna et al. |
| 2010/0057084 A1 | 3/2010 | Hanna et al. |
| 2010/0063500 A1 | 3/2010 | Muszala et al. |
| 2010/0069903 A1 | 3/2010 | Allen, IV et al. |
| 2010/0069904 A1 | 3/2010 | Cunningham et al. |
| 2010/0069953 A1 | 3/2010 | Cunningham et al. |
| 2010/0076427 A1 | 3/2010 | Heard et al. |
| 2010/0076430 A1 | 3/2010 | Romero et al. |
| 2010/0076431 A1 | 3/2010 | Allen, IV et al. |
| 2010/0076432 A1 | 3/2010 | Horner et al. |
| 2010/0087816 A1 | 4/2010 | Roy et al. |
| 2010/0094287 A1 | 4/2010 | Cunningham et al. |
| 2010/0100122 A1 | 4/2010 | Hinton et al. |
| 2010/0145334 A1 | 6/2010 | Olson et al. |
| 2010/0179545 A1 | 7/2010 | Twomey et al. |
| 2010/0179546 A1 | 7/2010 | Cunningham et al. |
| 2010/0179547 A1 | 7/2010 | Cunningham et al. |
| 2010/0249776 A1 | 9/2010 | Kerr et al. |
| 2010/0256635 A1 | 10/2010 | McKenna et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| EP | 1769766 | 4/2007 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; Vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group. (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l. Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
U.S. Appl. No. 12/336,9720, filed Dec. 17, 2008, Sremcich et al.

* cited by examiner

CUTTING ASSEMBLY FOR SURGICAL INSTRUMENTS

BACKGROUND

1. Technical Field

The present disclosure relates to surgical instruments. More particularly, the present disclosure relates to surgical instruments having cutting assemblies for cutting tissue.

2. Description of the Related Art

In many surgical procedures, tubular body tissue, for example, blood vessels, ducts, adhesions, fallopian tubes, are sealed to defunctionalize or close the tubular tissue. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heat processes have been employed.

In addition to closing tissue, in many situations it is necessary to cut tissue. Since forceps utilizes mechanical action to constrict, grasp, dissect and/or clamp tissue, it is particularly useful to also provide a cutting assembly within a forceps. Current tissue cutting procedures utilize, for example, knife assemblies and electrical cutting assemblies.

SUMMARY

The present disclosure relates to an end effector assembly for use with a forceps. The end effector assembly includes a pair of jaw members and a cutting element. The pair of jaw members having at least one jaw member that is moveable relative to the other from a first, open position to a second, closed position for grasping tissue. Each of the jaw members includes a cutting channel that is defined therein and extends therealong. The cutting element includes a fixed end and a movable end. The fixed end is disposed within the cutting channel of one of the jaw members and the moveable end is disposed within the cutting channel of the other of the jaw member. The cutting element defines a movable cutting loop disposed between the cutting channels and between the fixed end and the movable end. The cutting loop has an arcuate portion that is reciprocatable to cut tissue.

The present disclosure also relates to a forceps that includes a housing that has a shaft which extends therefrom having an end effector assembly engaged to a distal end thereof. An actuator is operably coupled to the end effector assembly. The end effector assembly includes a pair of jaw members and a cutting element. The pair of jaw members has at least one jaw member that is operably coupled to the actuator to move one of the jaw members relative to the other jaw member from a first, open position to a second, closed position for grasping tissue. Each of the jaw members includes a cutting channel defined therein that extends therealong. The cutting element includes a fixed end and a movable end. The fixed end is disposed within the cutting channel of one of the jaw members and the moveable end is disposed within the cutting channel of the other of the jaw members. The cutting element defines a movable cutting loop disposed between the cutting channels and between the fixed end and the movable end. The cutting loop has an arcuate portion that is reciprocatable to cut tissue.

BRIEF DESCRIPTION OF THE DRAWINGS

Various embodiments of the presently disclosed shroud is described herein with referent to the drawings, wherein.

DETAILED DESCRIPTION

Embodiments of the presently disclosed electrosurgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1:
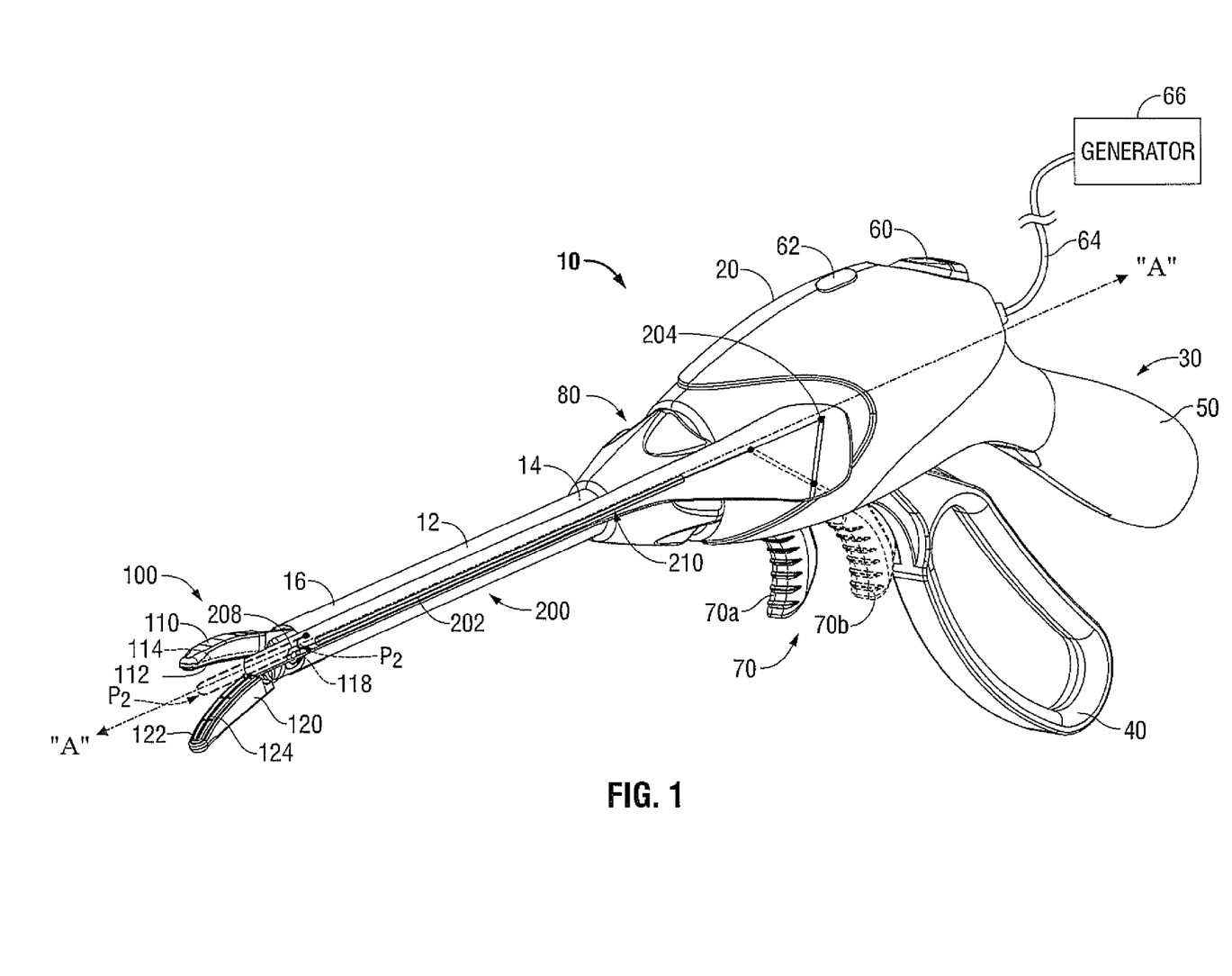
FIG. 1 is a perspective view of a surgical instrument having an end effector assembly in accordance with an embodiment of the present disclosure having a cut-out view that shows the components of a cutting assembly.

Turning now to FIG. 1, a bipolar forceps 10 is shown for use with various endoscopic or laparoscopic surgical procedures and generally includes a housing 20, a handle assembly 30, a trigger assembly 70, a rotating assembly 80, first and second switch assemblies 60 and 62, respectively, and an end effector assembly 100. Although the majority of the figure drawings depict a bipolar forceps 10 for use in connection with endoscopic surgical procedures, the present disclosure may be used with other suitable types of surgical instruments, such as, open surgical instruments.

Rotating assembly 80 is operatively connected to the housing 20 and is rotatable in either direction about a longitudinal axis "A" that is defined through shaft 12. Handle assembly 30 includes a fixed handle 50 and a movable handle 40. Fixed handle 50 is integrally associated with housing 20 and handle 40 is movable relative to fixed handle 50 to actuate jaw members 110 and 120 of the end effector assembly 100.

As shown in the figures and as will be described in the present disclosure, different embodiments of a novel cutting assembly are utilized with a combination of end effector assemblies, which may be positioned on different types of surgical instruments, for example, but not limited to, forceps 10 (as shown in FIG. 1). In the example embodiment of FIG. 1, end effector assembly 100 is positioned on the distal end 16 of shaft 12 and includes a pair of opposing jaw members 110 and 120 that cooperate to effectively grasp tissue and, for example, but not limited to, seal tissue. The end effector assembly 100 may be configured to operate as a unilateral assembly (as shown in FIG. 2C), whereby jaw member 120 is fixed (i.e., stationary) relative to the shaft 12 and jaw member 110 pivots about a pivot pin (not explicitly shown) relative to jaw member 120 to grasp tissue. Alternatively, the end effector assembly 100 may be configured to operate as a bilateral assembly (as shown in FIG. 1), whereby jaw members 110 and 120 both pivot about pivot pin 108 relative to each other to grasp tissue.

Each of the jaw members include tissue contacting surfaces 112 and 124, respectively, that have longitudinally-orientated channels 114 and 124, respectively, defined therethrough (See FIGS. 1 and 2A-2C). The channels 114 and 124 are configured to mutually align when the jaw members 110 and 120 are in both open and closed positions. Each of the channels 114 and 124 also include base portions 116 and 126 (as shown in FIGS. 2A, 3B, 4B, and 7A) that are configured to contain a cutting element 202 within the channels 114 and 124. In some embodiments, the base portions 116 and 126 have walls 117 and 127 on each side that are configured to contain cutting element 202 within the channels 114 and 124 (See FIGS. 3A-3B and 4A-4B).

Figure 4A:
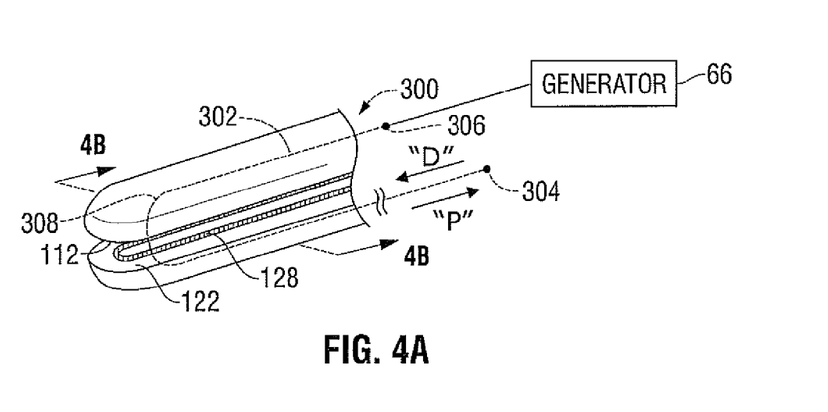
FIG. 4A is a perspective view of an end effector assembly having an energized cutting assembly in accordance with an embodiment of the present disclosure.
Figure 4B:
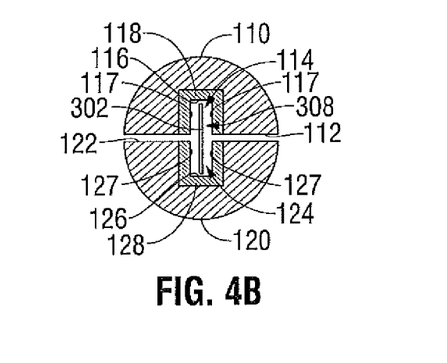
FIG. 4B is a cross-sectional view along lines 4B of the end effector assembly of FIG. 4A.

In some embodiments, first and second switch assemblies 60 and 62 are configured to selectively provide electrical energy to the end effector assembly 100. More particularly, the first switch assembly 60 is configured to selectively supply electrical energy to tissue contacting surfaces 112 and 122 and second switch assembly 62 is configured to selectively provide electrical energy to cutting element 302, as shown in FIGS. 4A and 4B and as will be discussed in further detail below. A cable 64 connects the forceps 10 to a source of electrosurgical energy, for example, but not limited to, an electrosurgical generator 66. Cable 64 is internally divided (not shown) within the handle assembly 30 and the shaft 12 to transport electrosurgical energy through various conductive paths and ultimately to end effector assembly 100. In this manner, the end effector assembly 100 may electrosurgically treat tissue.

Figure 2A:
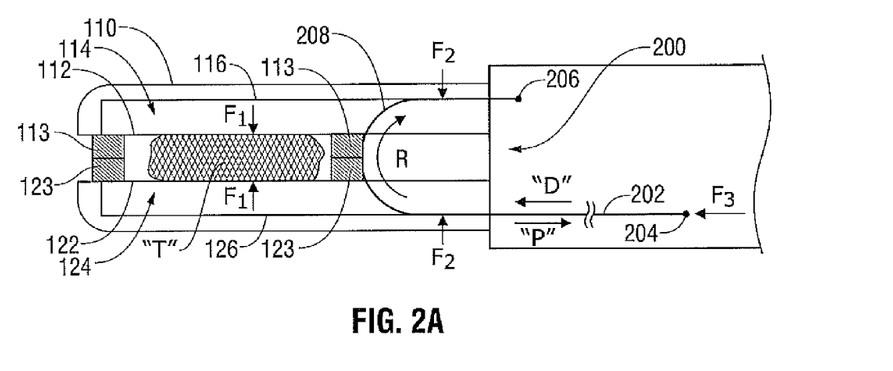
FIG. 2A is a side, cross-sectional view of the presently disclosed end effector assembly and cutting assembly of FIG. 1.
Figure 2B:
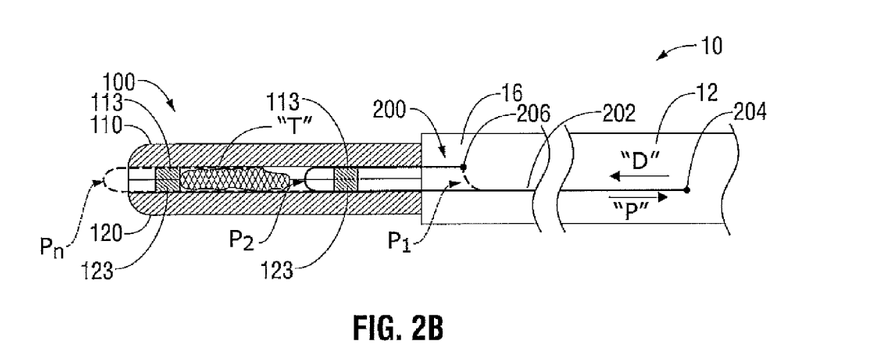
FIG. 2B is a side, cross-sectional view of the end effector assembly of FIG. 2A shown in a closed position and having tissue therebetween.
Figure 2C:
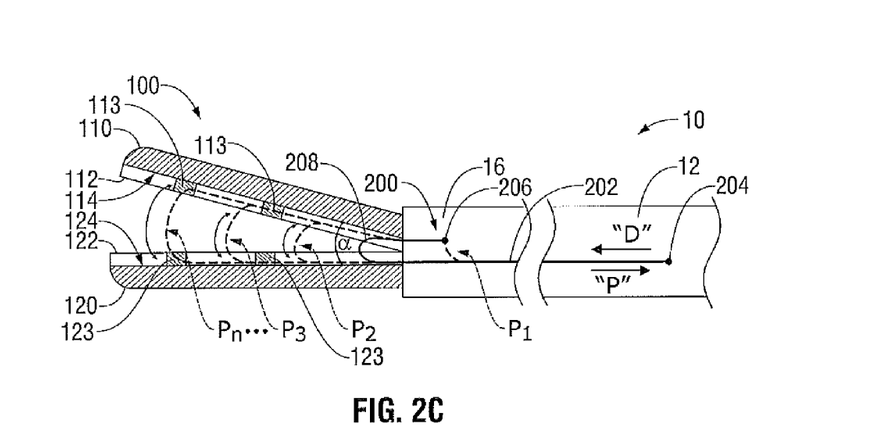
FIG. 2C is a side, cross-sectional view an end effector assembly shown in an open position.

Turning now to FIGS. 2A-2C, the end effector assembly 100 is shown incorporating a cutting assembly 200. In the illustrated embodiment, cutting assembly 200 includes cutting element 202 that includes a moving end 204 and a fixed end 206. Moving end 204 is positioned on a bottom portion of shaft 12 and then bent back, in a looping manner, such that the fixed end 206 is positioned on the top portion of the shaft 12. In this configuration, the cutting element 202 defines a moving cutting loop 208 as cutting element 202 is moved distally within shaft 12.

More particularly, the moving end 204 is configured to axially move along the longitudinal axis "A" in a proximal and distal direction, indicated by directional arrows "P" and "D", respectively. For example purposes, the fixed end 206 is shown positioned within "top" jaw member 110 and on the top portion of shaft 12 and the moving end 204 is shown positioned within "bottom" jaw member 120 and on the bottom portion of shaft 12. However, the moving end 204 may be positioned on either of the jaw members 110, 120 and top and bottom portions of forceps 10. Accordingly, the fixed end 206 is positioned on the opposite side of the moving end 204. As the moving end 204 is axially moved (i.e., rolled) in the proximal or distal direction, "P" and "D," the cutting loop 208 is variably positioned between the moving end 204 and the fixed end 206. The cutting loop 208 has an arcuate portion "R" that is determined by the position of the jaw members 110 and 120, which will described in detail further below.

The cutting element 202 may be, for example, but not limited to a wire or any other suitable bendable material. It is envisioned that cutting element 202 has structural properties of a constant form, for example, a rigid material. Alternatively, the cutting element may have structural properties varying in form, for example, a hybrid of rigid and flexible material.

In use, as shown in FIG. 2A, tissue "T" is held between the tissue contacting surfaces 112 and 122 by a compression force F1 that is exerted by the jaw members 110 and 120. The compression force F1 may be regulated by the closure of the handle 40 relative to handle 50 and one or more compression springs such that a predetermined force may be applied. A series of stop members 113 and 123 may be included to control the gap distance between jaw members 110 and 120. The cutting element 202 is held within the base portions 116 and 126 of channels 114 and 124, respectively, by a compression force F2 that is exerted by the jaw members 110 and 120. The compression force F2 is a predetermined force that is configured by the predetermined dimensions of the cutting element 202 and the channels 114 and 124. When the cutting element 202 is moved axially in a distal direction "D," a deployment force F3 is exerted by an actuation mechanism, for example, trigger assembly 70, such that movable end 204 is axially moved in a distal direction "D," thereby creating the moving cutting loop 208 that operates to sever tissue "T" between jaw members 110 and 120. The cutting loop 208 may also be referred to as a cutting edge that facilitates cutting tissue "T."

Effective cutting is accomplished by selecting the material and geometric properties of the cutting element 202 so as to control the deformation force reactions as the cutting loop 208 contacts the tissue "T" to be cut. Tissue "T" is grasped and compressed within the vicinity of the cutting element 202. As the movable end 204 of cutting element 202 is deployed in a distal direction "D," the cutting loop 208 contacts the tissue "T." In this manner, a mechanical transfer of energy occurs such that the deployment force F3 of movable end 204 is transferred to the bending cutting loop 208, which in turn, is transferred to the attachment end 206. All of these combined forces create a resistance that is felt by a clinician, while applying pressure to trigger assembly 70. In addition, the resistance gives a clinician a tactile feel of the cutting progress of tissue "T," as the cutting element 202 is deployed. The contact pressure between the tissue "T" and the cutting element 202 defines a function that is a product of a variety of contributing factors. These factors may include, but not limited to, tissue shear strength, tissue to cutting element contact area, a diameter of the cutting element 202, an arcuate portion of cutting loop 208, material properties of cutting element 202, effectiveness of the sharpened cutting edge (if any), effectiveness of the electrosurgical cutting effect (if any), and any coatings applied to cutting element 202.

As best shown in FIG. 1, a tubular sheath 210 surrounds cutting element 202 along the shaft 12. In this arrangement, the cutting element 202 is supported by the tubular sheath 210 when a clinician utilizes trigger assembly 70, which, in turn, moves cutting element 202 in a proximal direction "P" or distal direction "D". Additionally or alternatively, the tubular sheath 210 may also include a lubricious coating to facilitate movement of the cutting element 202 as it is moved along the shaft 12.

With respect to a non-sharpened cutting wire, if a sufficient deployment force F3 is generated such that cutting loop 208 overcomes the shear strength of the tissue "T", the cutting loop 208 will proceed to shear the tissue "T" as it is deployed therethrough. It should be noted that the "shearing" or "cutting" effect of cutting loop 208 may be further enhanced by the motion of cutting loop 208 introducing a transverse contact shear (i.e., perpendicular to the tissue contact surfaces 112 and 122) to the tissue "T" from frictional coefficient differences between the surface of the cutting element 202 and the tissue "T". The resultant motion of the cutting element 202 produces a "cut" of the tissue "T". It should be noted that cutting will continue as long as the force to shear the tissue "T" remains lower than the force to cause buckling of the cutting loop 208 and/or cutting element 202. The deployment force F3 of cutting loop 208 does not have to be constant at all times. However, the deployment force F3 of cutting loop 208 should be stable enough to prevent buckling of cutting element 202 which would, in turn, interrupt progression of the cutting loop 208 through the tissue "T" while movable end 204 is deployed. When utilizing a sharpened cutting element 202 or when utilizing an electrosurgical cutting effect many of these factors are reduced.

As shown in FIG. 2B, cutting element 202 is moved through jaw members 110 and 120 when in a closed position and having tissue "T" therebetween. For example, the cutting element 202 is deployed (i.e., rolled) from position P1 to position P2, and then to position Pn. As the cutting element 202 is deployed from position P2 to position Pn, the cutting loop 208 "cuts" or "shears" tissue "T," as described above. When the jaw members 110 and 120 are in the closed position the cutting loop 208 is maintained at a constant arcuate portion "R".

Alternatively, as shown in FIG. 2C, when the jaw members 110 and 120 are in an open position or partially open position, the arcuate portion "R" will vary in accordance with an angle α defined by the opening of jaw members 110 and 120. The cutting element 202 is shown having various positions throughout the end effector 100. For example, the cutting element 202 is deployed (i.e., rolled) from position P1 to positions P2, P3, to Pn. As the cutting element 202 is axially deployed in a distal direction "D" from starting position P1 to position Pn, the arcuate portion "R" increases when the jaw members 110 and 120 are in the open position.

When the cutting loop 208 is extended beyond the distal end of the jaws 110 and 120 the projecting cutting loop 208 may act as an extended monopolar or bipolar electrode for various electrosurgical procedures. In other embodiments, the extended loop embodiment described above also may be used as a mechanical snare for capturing a desired tissue about its volume using an internal section formed by the cutting loop 208 as the cutting element 202 is axially deployed in a distal direction "D" and retracted in a proximal direction "P" by a clinician. The cutting loop or cutting edge 208 facilitates cutting tissue when the mechanical snare is retracted. The mechanical snare is adapted to connect to an electrical energy source to facilitate cutting tissue.

Figure 3A:
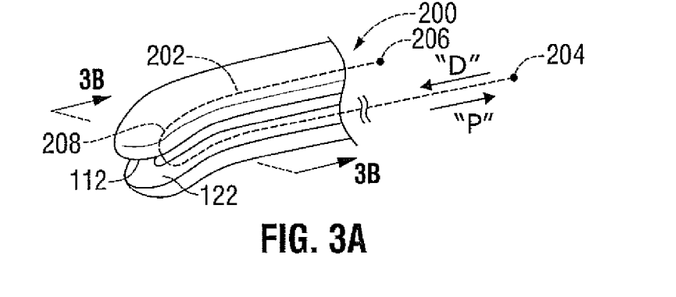
FIG. 3A is a perspective view of a curved end effector assembly in accordance with an embodiment of the present disclosure.
Figure 3B:
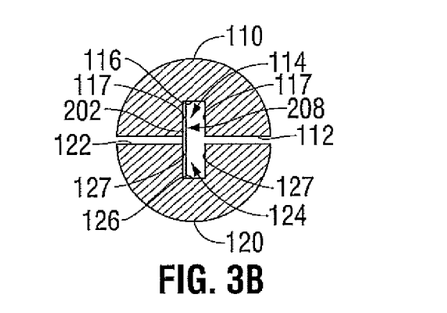
FIG. 3B is a cross-sectional view along lines 3B of the end effector assembly of FIG. 3A.

Referring now to FIGS. 3A and 3B, end effector assembly 100 is shown having curved jaw members 110 and 120. In this configuration, the cutting element 202 is configured to roll along the curved channels 114 and 124 and, therefore, along the curved jaw members 110 and 120. As the cutting element 202 is rolled along the curved channels 114 and 124, the cutting element 202 is rolled against one of the walls 117 and 127 to facilitate curved movement of the cutting element 202.

Referring now to FIGS. 4A and 4B, end effector assembly 100 is shown having a cutting assembly 300 that is selectively and electrically energized by a clinician and/or a programmable electrosurgical energy source, for example, but not limited to, generator 66. The selectively energized cutting assembly 300 is coupled to the electrosurgical generator 66 via cable 64, as described above. Similarly to cutting assembly 200, the selectively energized cutting assembly 300 includes a cutting element 302, a movable end 304, a fixed end 306, and a cutting loop 308.

Cutting element 302 is positioned within the end effector assembly 100 and forceps 10 in a similar manner that cutting element 202 is positioned in, as described above. As the moving end 304 of cutting element 302 is moved in a proximal direction "P", the cutting loop 308 is translated in a proximal direction "P". When jaw members 110 and 120 grasp tissue "T" therebetween, the cutting loop 308 is configured to selectively electrically cut the tissue "T." Additionally and alternatively, the cutting element 302 may be utilized in the same manner as described above such that the cutting element 302 selectively cuts tissue "T" without being electrically energized. High voltage/high frequency and resistance cutting may be combined simultaneously. Channels 114 and 124 may be insulated from cutting element 302 by insulators 118 and 128. In this manner, when cutting element 302 is energized, the electrical energy is isolated within insulators 118 and 128 and does not conduct to other parts of jaw members 110 and 120.

Figure 5A:
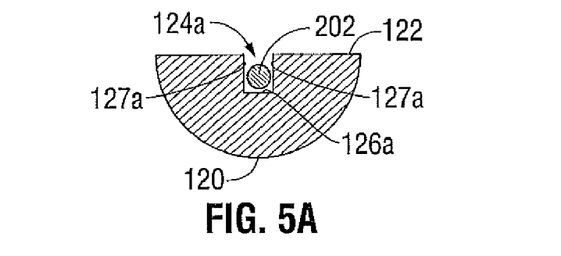
FIGS. 5A-5E are front, cross-sectional views of different embodiments of the presently disclosed end effector assemblies.

As best shown in FIGS. 5A-5E, example embodiments are shown to include varying cross-sections of channels 114 and 124. For example, FIG. 5A illustrates another embodiment of the channel 124a dimensioned to provide a substantially "exact" fit with cutting element 202 when deployed therethrough. In other words, base portion 126a and walls 127a are dimensioned to contain the cutting element 202 such that the cutting element 202 does not have any "play." In this manner, when the cutting element 202 is moved in either the proximal direction "P" or distal direction "D," a "twisting" or torsional force is applied against base portion 126a and walls 127a such that the cutting element 202 has a tight fit. It is also envisioned that in this embodiment a lubricious coating may be applied to the cutting element 202. Alternatively, a lubricous material may be expelled into the channels 114 and 124 via lubrication ports (not shown). For example, chromium nitride or a similar coating may be applied to the cutting element 202 to increase lubricity and/or reduce tissue sticking during or after the cutting process. It is also envisioned that chromium nitride may also be used for preventing corrosion.

Figure 5B:
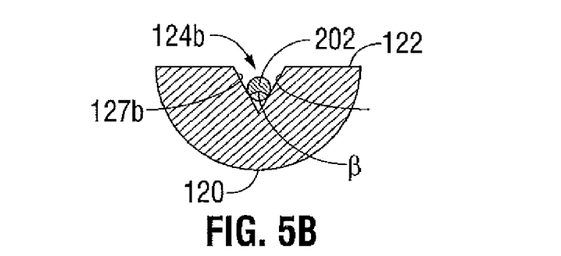
Figure 5C:
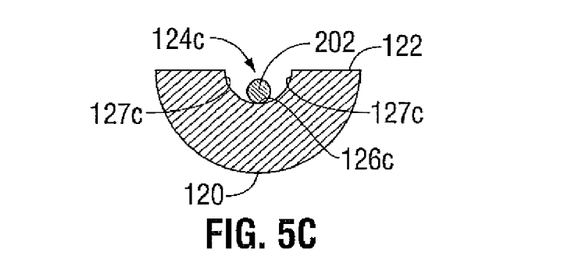
Figure 5D:
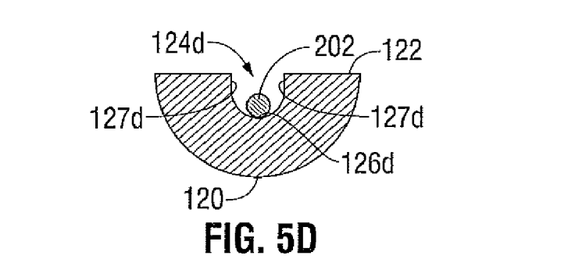
Figure 5E:
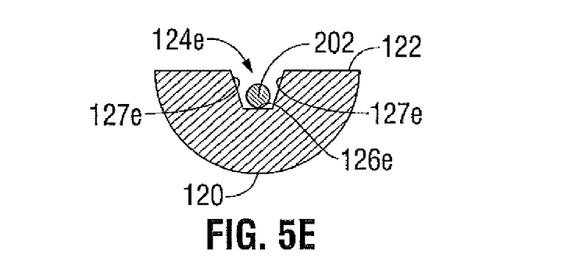

FIG. 5B illustrates another embodiment of the channel 124b having a triangular or "V-shaped" cross-section. In this embodiment, the base portion is eliminated and walls 127b converge at a predetermined angle β. Angle β may be configured to be any suitable degree. FIG. 5C illustrates a channel 124c having an oval configuration, while FIG. 5D illustrates channel 124d is shown having a circular configuration. Additionally, FIG. 5E illustrates another embodiment of channel 124e having a trapezoidal configuration. It is envisioned that the channels of the present disclosure may have any suitable polygonal shape.

Figure 6:
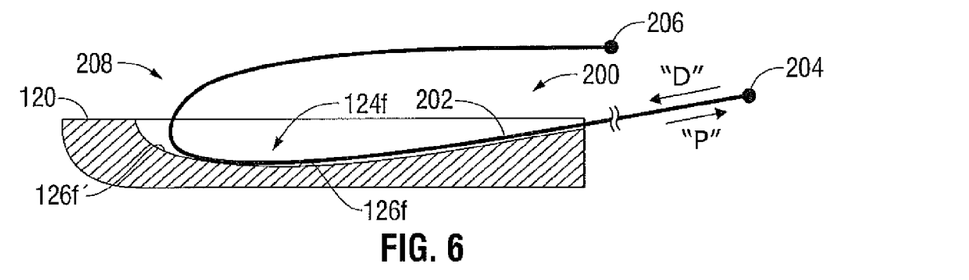
FIG. 6 is a side, cross-sectional view of another embodiment of the presently disclosed end effector assembly.

Turning now to FIG. 6, another embodiment of channel 124f is shown having a curved bottom portion 126f. Bottom portion 126f has a varying profile, but contains no inflections of curvature. In other words, the curvature change direction is always in same vector direction. In this manner, the cutting element 202 is in a constant buckling mode and in contact with base portion when axially rolled in a distal direction "D." The contact force and buckling is assisted by a biasing characteristic in bending of the cutting element 202. In addition, the biasing characteristic also makes the cutting element 202 contact the base portion 126f of the channel 124f due to the structural bending forces of forming the cutting element 202 path during deployment in the distal direction "D." A distal end 126f′ of bottom portion 126f may be curved or ramped to facilitate buckling of the cutting element 202 and transition of the cutting loop 208 towards the fixed end 206.

Figure 7A:
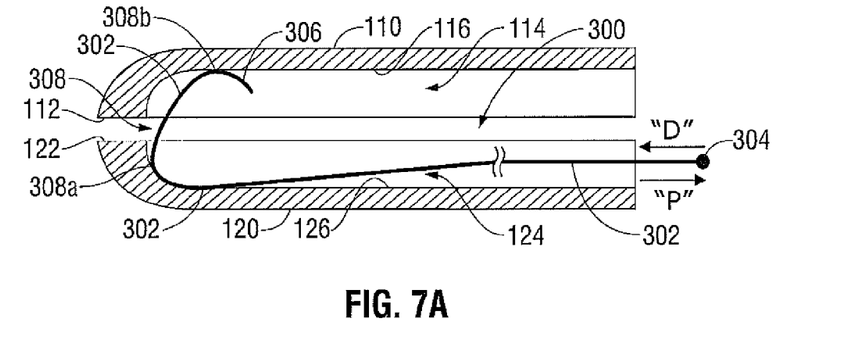
FIG. 7A is a side, cross-sectional view of another embodiment of the presently disclosed cutting element.

Turning now to FIG. 7A, cutting assembly 300 includes a cutting element 302 having a proximal end 304, a distal end 306, and a cutting edge 308 that is defined between the proximal and distal end 304 and 306. In this embodiment, cutting element 302 does not have a fixed end. Instead, cutting element 302 has a distal end 306 that is axially moved in proximal and distal directions, "P" and "D," when proximal moving end 304 is actuated by an actuation mechanism, for example, trigger assembly 70 (shown in FIG. 1). Cutting edge 308 may have a plurality of loops, as shown in FIG. 7A, for example, a distal bottom loop 308a situated within channel 124 and a proximal top loop 308b situated within channel 114. Channels 114 and 124 are configured to stabilize cutting element 302 as it is moved axially within jaw members 110 and 120. Cutting edge 308 may take a variety of forms, for example, but not limited to, angled, blunt, serrated, and sharp.

Figure 7B:
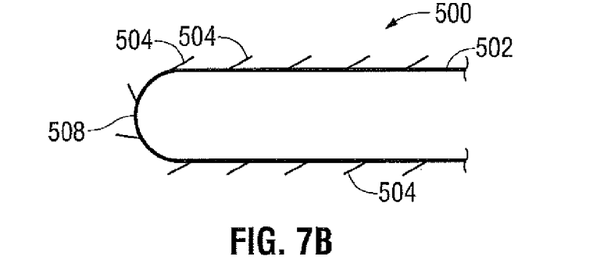
FIG. 7B is a schematic view of yet another embodiment of the presently disclosed cutting element.

Turning now to FIG. 7B, an example embodiment of a cutting assembly 500 is shown having a cutting element 502 that is composed of a plurality of sharp and/or rough edges 504. For example, cutting element 502 may be utilized as a "saw" edge. For example, when the cutting element 502 is an exposed position such that the jaw members 110 and 120 are in an open position, the cutting element 502 can be positioned on tissue in a manner to stroke against tissue to cut the tissue.

Figure 7C:
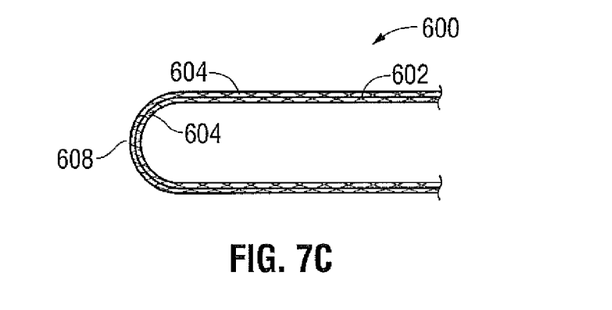
FIG. 7C is a schematic view of still another embodiment of the presently disclosed cutting element.

As best shown in FIG. 7C, an example embodiment of a cutting assembly 600 is shown having a cutting element 602 that is composed of a plurality of wires 604. Additionally or alternatively, cutting element 602 may be formed into a bundle of hollow tube composite cables or wires 604 by a suitable manufacturing technique. The plurality of wires 604 may contain conductive and non-conductive elements to suitably produce the desired mechanical and electrical properties. Also, each wire may have individual characteristics, for example, but not limited to, plurality of wires 604 may contain a mix of metallic and non-metallic fibers having insulating or lubricous coating thereon to aid in movement. It is envisioned the plurality of wires 604 may be varied, intermittent, or continuous along the length of the cutting element 602 and at a suitable length and/or location to adequately aid in the desired cutting effect. It is also envisioned that cutting element 602 may include a bundle of tubular wire-like elements.

It is envisioned that a clinician may return the cutting element 202 to a position near the distal end 16 of shaft 12, for example, position P1 (as shown in FIGS. 2B and 2C), in order to restore the cutting element's 202 position within the channels 114 and 124, such as, in a case where accidental slippage of the cutting element 202 out of the channels 114 and 124 has occurred. The structural flexure properties of the smaller loop, at position P1, create a stiffer cutting loop 208 form and consequently self-center (i.e., restore) the cutting element 202 within the jaw members 110 and 120.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly for use with a forceps, the end effector assembly comprising:
    a pair of jaw members, at least one jaw member moveable relative to the other from a first, open position to a second, closed position for grasping tissue, each of the jaw members including a cutting channel defined therein that extends therealong; and
    a cutting element including a fixed end and a movable end, the fixed end disposed within the cutting channel of one of the jaw members and the moveable end disposed within the cutting channel of the other of the jaw members, the cutting element defining a movable cutting loop disposed between the cutting channels and between the fixed end and the movable end, said cutting loop having an arcuate portion that is reciprocatable to cut tissue, wherein the at least one cutting channel includes a ramped distal end to facilitate transition of the cutting loop toward the fixed end.

2. An end effector assembly for use with a forceps, the end effector assembly comprising:
    a pair of jaw members, at least one jaw member moveable relative to the other from a first, open position to a second, closed position for grasping tissue, each of the jaw members including a cutting channel defined therein that extends therealong; and
    a cutting element including a fixed end and a movable end, the fixed end disposed within the cutting channel of one of the jaw members and the moveable end disposed within the cutting channel of the other of the jaw members, the cutting element defining a movable cutting loop disposed between the cutting channels and between the fixed end and the movable end, said cutting loop having an arcuate portion that is reciprocatable to cut tissue, wherein at least one cutting channel includes a curved bottom portion having a varying profile such that the cutting element remains in contact with a base portion when reciprocated.

* * * * *